US010303850B2

(12) United States Patent
Kurami et al.

(10) Patent No.: US 10,303,850 B2
(45) Date of Patent: May 28, 2019

(54) MEDICAL ASSISTANCE DEVICE, OPERATION METHOD AND PROGRAM FOR MEDICAL ASSISTANCE DEVICE, AND MEDICAL ASSISTANCE SYSTEM FOR TEMPORARY MEDICAL INFORMATION DISPLAY WITH POINTER-OVER OPERATION

(71) Applicant: FUJIFILM Corporation, Tokyo (JP)

(72) Inventors: Yoshiyuki Kurami, Kanagawa (JP); Akinari Tsugo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 109 days.

(21) Appl. No.: 14/751,160

(22) Filed: Jun. 26, 2015

(65) Prior Publication Data
US 2016/0019358 A1    Jan. 21, 2016

(30) Foreign Application Priority Data

Jul. 15, 2014    (JP) .................................. 2014-145097

(51) Int. Cl.
*G06F 3/048*    (2013.01)
*G06Q 50/00*    (2012.01)
(Continued)

(52) U.S. Cl.
CPC ............ *G06F 19/34* (2013.01); *G06F 3/0481* (2013.01); *G06F 16/248* (2019.01);
(Continued)

(58) Field of Classification Search
CPC . G06F 3/048; G06F 3/00; G06F 17/00; G06F 19/00; G06F 19/34; G06F 17/30; G06Q 50/24; G06Q 30/00; G06Q 50/00
See application file for complete search history.

(56) References Cited

U.S. PATENT DOCUMENTS 6,611,846 B1 *    8/2003    Stoodley ............... G06F 19/322
                                                      705/3
9,665,957 B1 *    5/2017    Davis ................... G06F 11/3409
(Continued)

FOREIGN PATENT DOCUMENTS

JP    H2-228522    9/1990
JP    2009-064354    3/2009
(Continued)

OTHER PUBLICATIONS

"Office Action of Japan Counterpart Application", dated Sep. 21, 2016, with machine English translation thereof, pp. 1-7.
(Continued)

*Primary Examiner* — Hugo Molina
(74) *Attorney, Agent, or Firm* — JCIPRNET

(57) ABSTRACT

An item name display region where item names of a plurality of items included in the medical information of a patient are displayed and a content display region where a graph for each item is displayed are provided on a display screen of a medical assistance client. On the display screen, a display/non-display setting of the graph for each item is possible in the content display region by a first operation including a mouse click operation. The graph of a non-display setting item can be temporarily displayed by a mouse-over operation not including the click operation. The mouse-over operation is an operation of just overlapping a pointer on the item name display region.

13 Claims, 12 Drawing Sheets

(51) Int. Cl.
*G06F 19/00* (2018.01)
*G06F 3/0481* (2013.01)
*G06F 16/2458* (2019.01)
*G06F 16/904* (2019.01)
*G06F 16/248* (2019.01)
*G06F 17/00* (2019.01)

(52) U.S. Cl.
CPC ........ *G06F 16/2477* (2019.01); *G06F 16/904* (2019.01); *G06Q 50/00* (2013.01); *G06F 17/00* (2013.01)

(56) References Cited

U.S. PATENT DOCUMENTS

| | | | | |
|---|---|---|---|---|
| 2007/0198301 | A1* | 8/2007 | Ayers | G06F 17/30554 705/3 |
| 2009/0024411 | A1* | 1/2009 | Albro | G06F 19/322 705/2 |
| 2010/0103177 | A1 | 4/2010 | Shinohara et al. | |
| 2010/0333024 | A1* | 12/2010 | Chan | G06F 17/30867 715/816 |
| 2011/0046974 | A1* | 2/2011 | Burks | G06Q 50/22 705/2 |
| 2014/0075380 | A1* | 3/2014 | Milirud | G06F 11/323 715/810 |
| 2014/0317130 | A1* | 10/2014 | Thope | G06F 16/245 707/754 |
| 2015/0006244 | A1* | 1/2015 | Tietzen | G06Q 30/0201 705/7.29 |
| 2015/0339868 | A1 | 11/2015 | Okuda et al. | |

FOREIGN PATENT DOCUMENTS

| | | |
|---|---|---|
| JP | 2011-150395 | 8/2011 |
| JP | 2014-096009 | 5/2014 |
| WO | 2008/126245 | 10/2008 |

OTHER PUBLICATIONS

"Office Action of China Counterpart Application," dated May 4, 2018, with English translation thereof, pp. 1-35.

* cited by examiner

FIG. 7

| ITEM | | | DISPLAY/NON-DISPLAY | |
|---|---|---|---|---|
| MAJOR CATEGORY | MIDDLE CATEGORY | SMALL CATEGORY | | 53A |
| VITAL | | BODY TEMPERATURE [°C] | ☑ DISPLAY | ☐ NON-DISPLAY |
| | | BLOOD PRESSURE (TOP) [mmHg] | ☑ DISPLAY | ☐ NON-DISPLAY |
| | | BLOOD PRESSURE (BOTTOM) [mmHg] | ☐ DISPLAY | ☑ NON-DISPLAY |
| | | PULSE RATE [TIMES]  53A | ☐ DISPLAY | ☑ NON-DISPLAY |
| | | BODY WEIGHT [kg] | ☐ DISPLAY | ☑ NON-DISPLAY |
| TEST SUBSTANCE EXAMINATION | BIOCHEMICAL | AST(GOT) [IU/l]  53A | ☐ DISPLAY | ☑ NON-DISPLAY |
| | | ALT(GPT) [IU/l] | ☐ DISPLAY | ☑ NON-DISPLAY |
| | | CREATININE [mg/dl] | ☐ DISPLAY | ☑ NON-DISPLAY |
| | | UREA NITROGEN [mg/dl] | ☐ DISPLAY | ☑ NON-DISPLAY |
| | | CRP [mg/dl] | ☐ DISPLAY | ☑ NON-DISPLAY |
| | | TOTAL BILIRUBIN [mg/dl] | ☐ DISPLAY | ☑ NON-DISPLAY |
| | BLOOD | WHITE BLOOD CELL COUNT [x1000/μl] | ☐ DISPLAY | ☑ NON-DISPLAY |
| | | HEMOGLOBIN [g/dl] | ☐ DISPLAY | ☑ NON-DISPLAY |

53

MEDICAL ASSISTANCE DEVICE, OPERATION METHOD AND PROGRAM FOR MEDICAL ASSISTANCE DEVICE, AND MEDICAL ASSISTANCE SYSTEM FOR TEMPORARY MEDICAL INFORMATION DISPLAY WITH POINTER-OVER OPERATION

CROSS-REFERENCE TO RELATED APPLICATIONS

The present application claims priority under 35 U.S.C. § 119 to Japanese Patent Application No. 2014-145097, filed on Jul. 15, 2014, all of which are hereby expressly incorporated by reference into the present application.

BACKGROUND OF THE INVENTION

1. Field of the Invention

The present invention relates to a medical assistance device to assist with a medical examination, an operation method and a non-transitory computer-readable recording medium storing a program for a medical assistance device, and a medical assistance system.

2. Description of the Related Art

In the medical field, a medical assistance system that assists with a medical examination by displaying medical information acquired during the diagnosis of a patient is known (refer to JP1990-228522A (JP-H02-228522A) and JP2011-150395A).

Medical information includes information regarding a wide range of items, such as items regarding vital signs including body temperature, blood pressure, and pulse or items regarding examinations, such as a biochemical test and a blood test. JP1990-228522A (JP-H02-228522A) discloses a display screen on which a plurality of items of medical information are displayed side by side. An item name display region for displaying item names and a content display region for displaying the data content of each item are provided on the display screen. In the content display region, time-series data in which medical information acquired by multiple measurements or examinations performed at different timings is recorded is displayed in the form of a graph or the like. The system disclosed in JP1990-228522A (JP-H02-228522A) has a display/non-display setting function for selecting items to be displayed on the display screen. Operation keys are disposed on the display screen, and items to be displayed among the plurality of items are set by the selection operation including an operation of pressing the operation keys (page 2, lower left field). Only the items selected by such a selection operation are displayed on the display screen, and the other items are not displayed on the display screen.

Similar to the display screen disclosed in JP1990-228522A (JP-H02-228522A), JP2011-150395A discloses a display screen on which the graphs of a plurality of items can be displayed side by side. On the display screen disclosed in JP2011-150395A, a graph that the pointer overlaps is highlighted by a mouse-over operation without a click operation. Here, the mouse-over operation is an operation of just overlapping the mouse pointer on any of the plurality of graphs that are displayed. Specifically, a graph that the pointer overlaps is emphasized since graphs other than the graph that the pointer overlaps are changed to a relatively light color (paragraph 0033). There is a wide range of items in the medical information, and the number of items is large even for the limited items that are required according to a patient or a disease. Therefore, when all of the items are displayed on the display screen, it is very difficult to see the items. For this reason, it is necessary to reduce the number of display items by selecting the display items using the display/non-display setting function disclosed in JP1990-228522A (JP-H02-228522A) or the like. Meanwhile, depending on the condition of a patient or the content or conditions of a disease, many of the items set so as not to be displayed need to be temporarily referred to. Needless to say, considering the visibility of the display screen, it is preferable that the item set so as not to be displayed is not displayed after the end of temporary reference.

However, the display/non-display setting function disclosed in JP1990-228522A (JP-H02-228522A) requires a selection operation including an operation of pressing the operation key for the setting of display and non-display. Therefore, there has been a problem that the operation is complicated when setting the non-display item as a display item temporarily or when returning the display item to the non-display item after the end of temporary reference. Also in JP2011-150395A, there is neither description nor suggestion on the above problem and the solution.

SUMMARY OF THE INVENTION

It is an object of the invention to provide a medical assistance device that enables temporary reference of an item, which is set so as not to be displayed, by a simple operation on a display screen where a plurality of items of medical information are displayed, an operation method and a non-transitory computer-readable recording medium storing a program for a medical assistance device, and a medical assistance system.

In order to solve the above described problem, a medical assistance device according to an aspect of the present invention includes a screen editing unit, a display/non-display setting unit, and a screen control unit. The screen editing unit edits a display screen for displaying medical information of a patient and sends an operation instruction by operating a pointer of a graphical user interface. The display screen has an item name display region where an item name of each of a plurality of items included in the medical information is displayed and a content display region where data content for each of the items is displayed. The display/non-display setting unit performs a setting regarding whether or not to display the data content of each of the items in the content display region in response to the operation instruction based on a first operation including a click operation of an operation unit of the pointer. The screen control unit performs control to display, for non-display setting items set so as not to be displayed among the items, the data content corresponding to the item name that the pointer overlaps in the content display region in response to the operation instruction based on a second operation not including the click operation and to return the data content to a non-display state when the pointer is removed from a position of the item name and the second operation has ended, the second operation being an operation of just overlapping the pointer on the position of the item name in the item name display region.

It is preferable that a collective display operation unit that inputs an operation instruction to collectively display the data content in the content display region for all of the non-display setting items while maintaining setting content of the non-display setting items set by the display/non-display setting unit is provided on the display screen.

It is preferable that the data content is time-series data for each of the items in which medical information of the patient is recorded in time series. It is preferable that the time-series data is displayed in a form of a graph. It is preferable that the items include items regarding vital signs and examinations.

It is preferable that, on the display screen, a plurality of the item names are arranged in a vertical direction in the item name display region, a time axis is set in a horizontal direction in the content display region, and the time-series data is displayed for each of the items.

It is preferable that when the non-display setting item is displayed by the second operation, data content of the non-display setting item and markings are displayed in the content display region.

An operation method of a medical assistance device according to another aspect of the invention includes a screen editing step, a display/non-display setting step, and a screen control step. In the screen editing step, a display screen is edited for displaying medical information of a patient and an operation instruction is sent by operating a pointer of a graphical user interface. The display screen has an item name display region where an item name of each of a plurality of items included in the medical information is displayed and a content display region where data content for each of the items is displayed. In the display/non-display setting step, a setting is performed regarding whether or not to display the data content of each of the items in the content display region in response to the operation instruction based on a first operation including a click operation of an operation unit of the pointer. In the screen control step, control is performed to display, for non-display setting items set so as not to be displayed among the items, the data content corresponding to the item name that the pointer overlaps in the content display region in response to the operation instruction based on a second operation not including the click operation and to return the data content to a non-display state when the pointer is removed from a position of the item name and the second operation has ended, the second operation being an operation of just overlapping the pointer on the position of the item name in the item name display region.

A medical assistance program according to still another aspect of the invention is a medical assistance program causing a computer to function as a medical assistance device, and cause a computer to execute a screen editing step, a display/non-display setting step, and a screen control step. In the screen editing step, a display screen is edited for displaying medical information of a patient and sending an operation instruction by operating a pointer of a graphical user interface, the display screen having an item name display region where an item name of each of a plurality of items included in the medical information is displayed and a content display region where data content for each of the items is displayed. In the display/non-display setting step, a setting is performed regarding whether or not to display the data content of each of the items in the content display region in response to the operation instruction based on a first operation including a click operation of an operation unit of the pointer. In the screen control step, control is performed to display, for non-display setting items set so as not to be displayed among the items, the data content corresponding to the item name that the pointer overlaps in the content display region in response to the operation instruction based on a second operation not including the click operation and to return the data content to a non-display state when the pointer is removed from a position of the item name and the second operation has ended, the second operation being an operation of just overlapping the pointer on the position of the item name in the item name display region.

A medical assistance system according to still another aspect of the invention is a medical assistance system formed by a medical assistance client and a medical assistance server, and includes a screen editing unit, a display/non-display setting unit, and a screen control unit. The screen editing unit edits a display screen for displaying medical information of a patient and sends an operation instruction by operating a pointer of a graphical user interface, the display screen having an item name display region where an item name of each of a plurality of items included in the medical information is displayed and a content display region where data content for each of the items is displayed. The display/non-display setting unit performs a setting regarding whether or not to display the data content of each of the items in the content display region in response to the operation instruction based on a first operation including a click operation of an operation unit of the pointer. The screen control unit performs control to display, for non-display setting items set so as not to be displayed among the items, the data content corresponding to the item name that the pointer overlaps in the content display region in response to the operation instruction based on a second operation not including the click operation and to return the data content to a non-display state when the pointer is removed from a position of the item name and the second operation has ended, the second operation being an operation of just overlapping the pointer on the position of the item name in the item name display region.

According to the invention, it is possible to provide the medical assistance device that enables temporary reference of an item, which is set so as not to be displayed, by a simple operation on a display screen where a plurality of items of medical information are displayed, the operation method and a non-transitory computer-readable recording medium storing a program for a medical assistance device, and the medical assistance system.

BRIEF DESCRIPTION OF THE DRAWINGS

FIG. 4 is a block diagram showing the electrical configuration of a computer that is used as a medical assistance server or the like.

FIG. 7 is an explanatory diagram of a display/non-display setting screen.

DESCRIPTION OF THE PREFERRED EMBODIMENTS

First Embodiment

Figure 1:
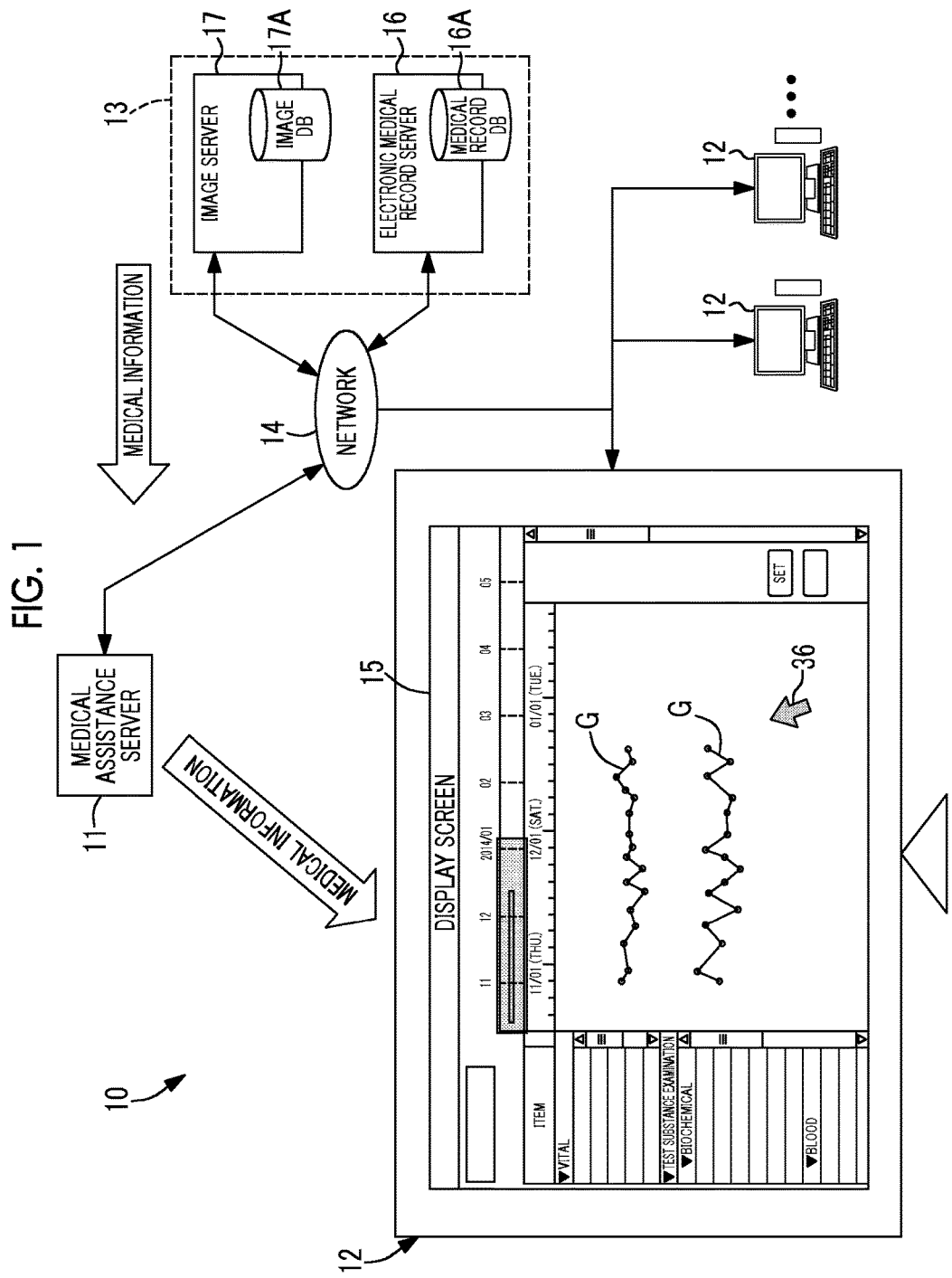
FIG. 1 is an explanatory diagram showing a medical information system.

A medical information system 10 shown in FIG. 1 is a computer system used for the management and use of medical information in medical facilities, such as a hospital. The medical information system 10 is configured to include a medical assistance server 11, a medical assistance client 12, a server group 13, and a network 14 that communicably connects these to each other. The server group 13 is a server that stores the medical information of a patient, and an electronic medical record server 16, an image server 17, and the like are included in the server group 13. The network 14 is a local area network (LAN) provided in the hospital, for example.

The medical assistance client 12 is a terminal installed in each department, such as internal medicine, surgery, otolaryngology, and ophthalmology, and is operated, for example, by the doctor of each department. The medical assistance client 12 has a function of accessing the electronic medical record server 16 to input or view electronic medical records. As the electronic medical records, medical information including medical examination records such as interview and diagnostic content, examination values of medical examinations or measurement values of vital signs, and treatment records such as treatment and surgery, is input. The medical assistance client 12 has a function of accessing the image server 17 to view examination images, such as X-ray images. Thus, the medical assistance client 12 functions as a viewer terminal for viewing the medical information.

In addition, the medical assistance client 12 has a function of accessing the medical assistance server 11 to receive the distribution of the medical information of a patient and display the distributed medical information on a display screen 15 so that the medical information can be viewed. Unlike a medical record display screen only for electronic medical records or an image display screen only for examination images, the display screen 15 can collectively display the examination values or measurement values of medical examinations and examination images, which are included in electronic medical records, on one screen. For example, when there is a plurality of examination values or a plurality of measurement values, these values are recorded in time series, and time-series data indicating the temporal changes in the examination values or the measurement values is displayed on the display screen 15 in the form of a graph G, for example. The display form of time-series data is not limited to a graph. For example, examination values or measurement values themselves may be arranged and displayed in the form of a table along the time axis.

The medical assistance server 11 acquires the medical information of a designated patient from the electronic medical record server 16 or the image server 17 in response to a distribution request including the designation of a patient from the medical assistance client 12. Then, the medical assistance server 11 distributes the acquired medical information to the requesting medical assistance client 12.

The electronic medical record server 16 includes an electronic medical record database (hereinafter, referred to as a medical record DataBase (DB)) 16A in which electronic medical records are stored. The image server 17 has an image DB 17A in which a plurality of examination images are stored, and is a so-called picture archiving and communication system (PACS) server. The medical record DB 16A or the image DB 17A is a database that can be searched using a keyword, such as patient identification data (ID).

Figure 2:
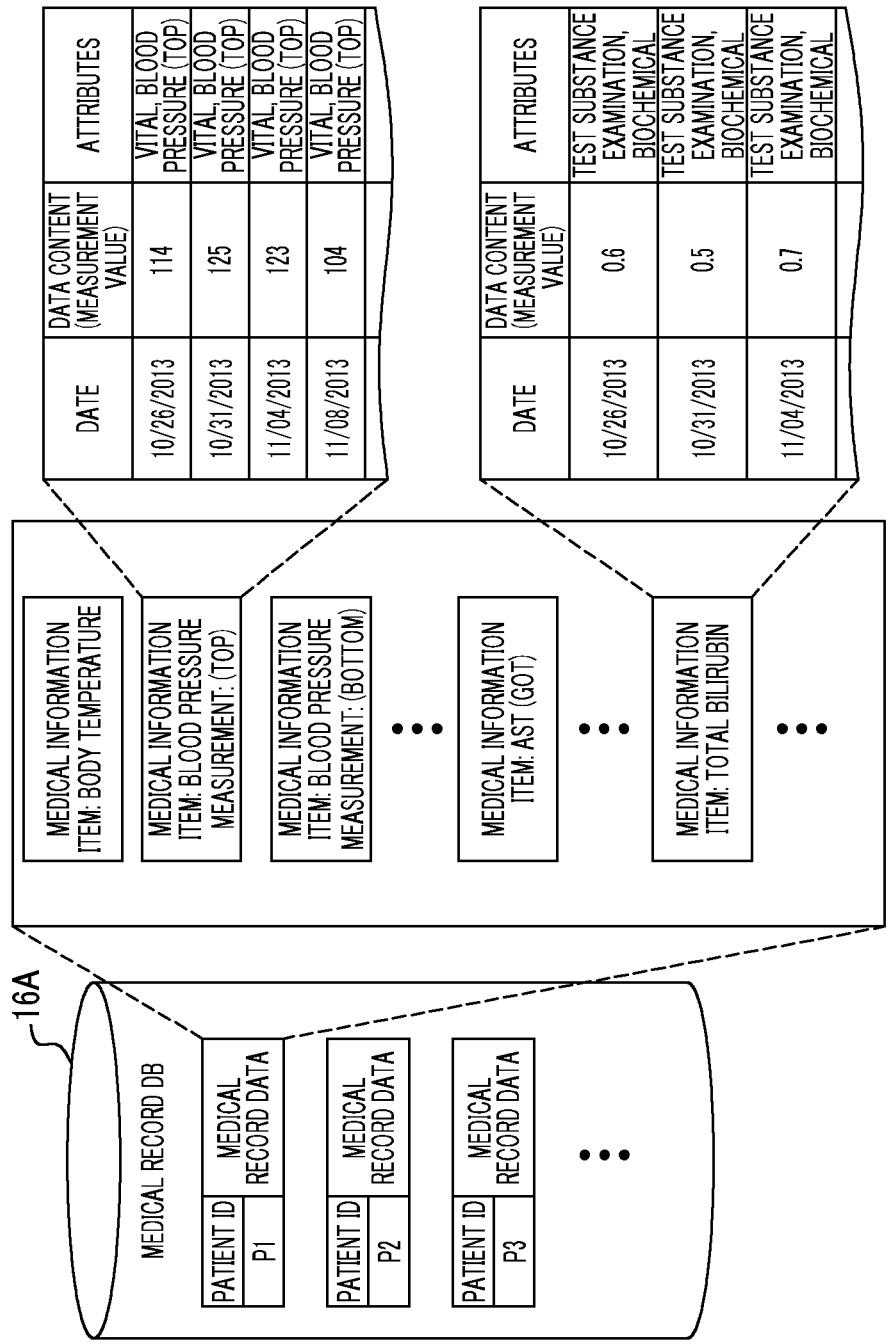
FIG. 2 is an explanatory diagram showing medical information recorded in the electronic medical record.

As shown in FIG. 2, medical record data in which the medical information of a patient is recorded is stored in the medical record DB 16A. Patient IDs (P1, P2, . . . ) are given to the medical record data, and the medical record data is managed in units of patients. The medical record data includes basic patient information, such as a patient's name, date of birth, sex, and a patient ID, and medical information of patients.

Measurement values of vital signs, such as a patient's heart rate, pulse, blood pressure, and body temperature, and examination values of clinical tests performed on the patient are included in the medical information. The clinical tests include test substance examinations, such as biochemical tests and blood tests, and physiological tests, such as electroencephalography. In addition, the content of a medical examination performed for a patient, specifically, the content of treatment, such as medication or surgery, and the content of the interview are included in the medical information. Thus, there is a plurality of items in the medical information. In FIG. 2, items, such as body temperature, measurement values of blood pressure (top) and blood pressure (bottom), AST: ASparTate aminotransferase (GOT: Glutamic Oxaloacetic Transaminase) as an examination value of a biochemical test, and total bilirubin, are illustrated as medical information.

For example, information regarding the date and time such as an examination date or a measurement date, acquired data content (examination values, measurement values, and the like), and attributes are included in the record for one case of each item of medical information. The information of date and time is measurement date and time in the case of a measurement value, and is examination date and time in the case of an examination value, and is dosing date and time or prescription date and time in the case of a dosage.

Attributes are information given to classify data, and is information indicating the attribute of each item of medical information. The attributes can also be used as a keyword for searching for the medical information. As attributes, for example, an item name ("blood pressure (top)", "dosing", and the like) of medical information and a category name to which an item belongs are included. As categories, for example, there are "vital", "test substance examination", and the like as major categories, and there are "biochemical test", "blood test", and the like as middle categories of the test substance examination.

Figure 3:
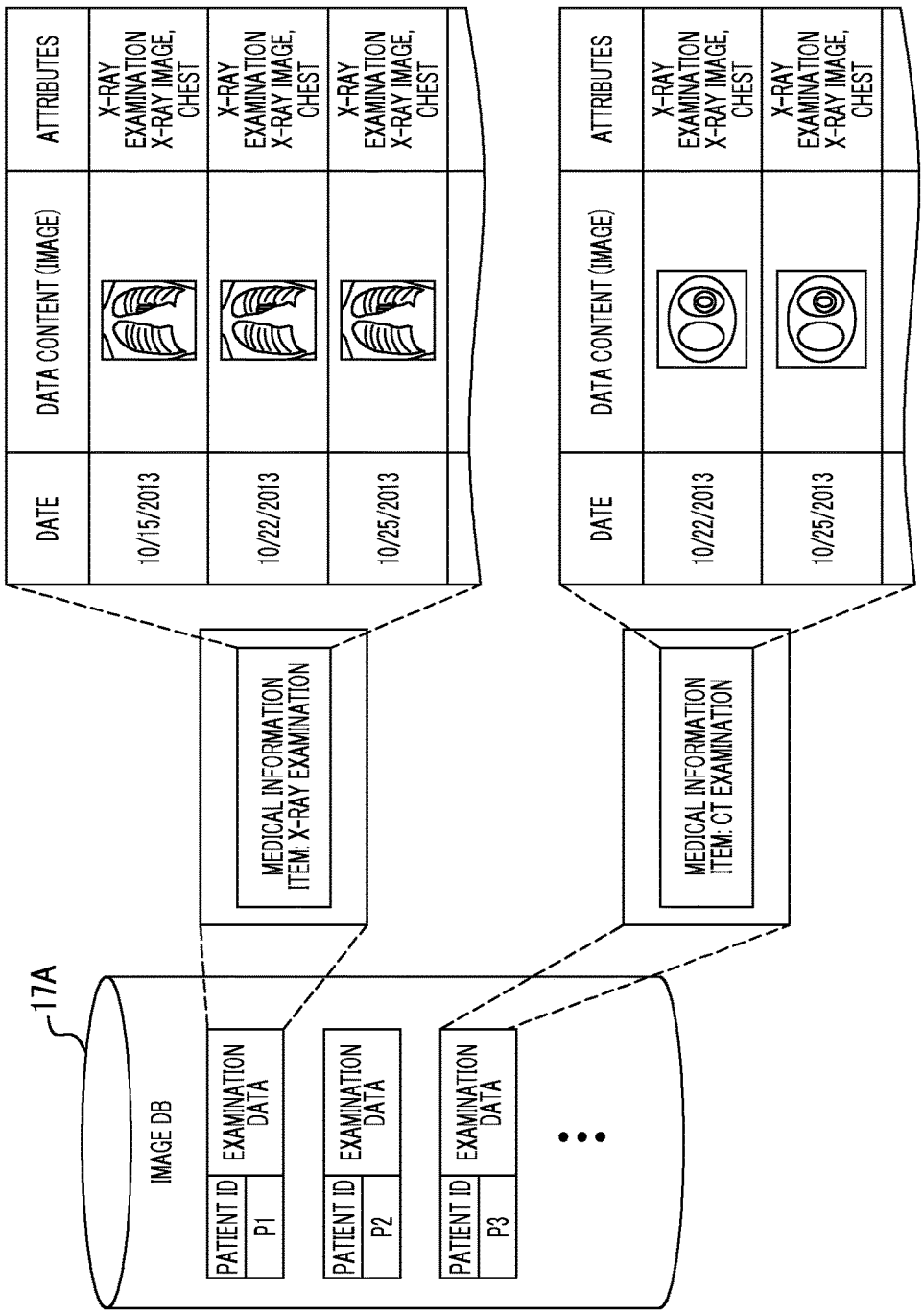
FIG. 3 is an explanatory diagram showing medical information recorded in an image server.

As shown in FIG. 3, examination data including a plurality of examination images captured by image examination, such as X-ray examination or CT examination, is stored in the image DB 17A. A patient ID is given to each examination image, so that the examination image can be searched for based on the patient ID. In the image examination, as a plurality of tomographic images obtained by computed tomography (CT) examination, a plurality of examination images may be captured in a single examination. The same examination ID is given to the plurality of examination images captured in a single examination, so that the plurality of examination images captured in a single examination is managed as examination images of one case. In addition, the examination images are also managed for each date and time in which image examination has been performed. As attributes of the examination image, for example, information, such as "X-ray examination" or "CT examination" indicating the examination type, "X-ray image" or "CT image" indicating the image type, and "chest" or "head" indicating the imaging part, is given.

The medical assistance server 11, the medical assistance client 12, the electronic medical record server 16, and the image server 17 are configured by installing a control program, such as an operating system, or an application program, such as a client program or a server program, on a computer, such as a personal computer, a server computer, or a workstation.

Figure 4:
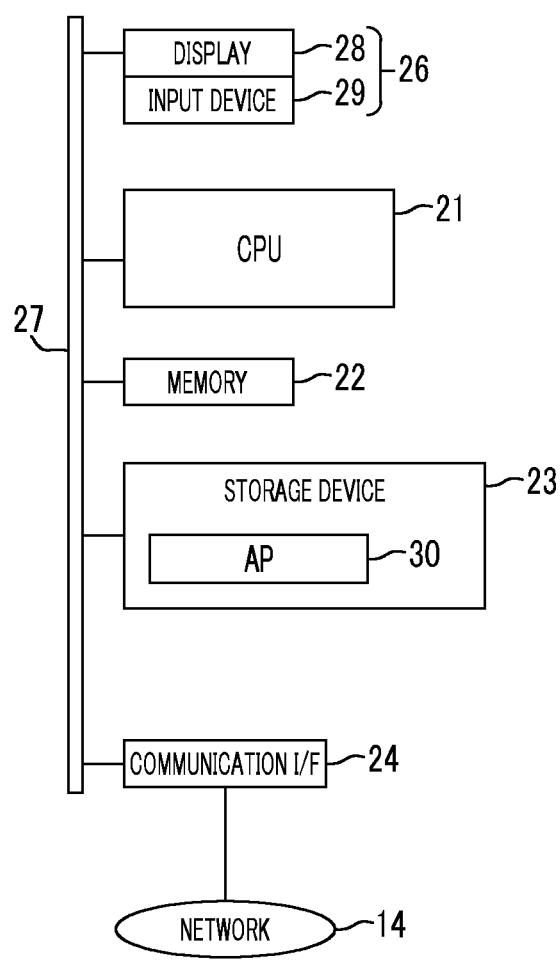

As shown in FIG. 4, computers that form the servers 11, 16, and 17 and the medical assistance client 12 have basically the same configuration. Each computer includes a central processing unit (CPU) 21, a memory 22, a storage device 23, a communication I/F 24, and an input/output unit 26. These are connected to each other through a data bus 27. The input/output unit 26 is configured to include a display (display unit) 28 and an input device 29, such as a keyboard or a mouse.

The storage device 23 is, for example, a hard disk drive (HDD), and a control program or an application program (hereinafter, referred to as an AP) 30 is stored in the storage device 23. In a server in which a DB is built, apart from the HDD to store a program, for example, a disk array formed by connecting a plurality of HDDs to each other is provided as the storage device 23 for a DB. The disk array may be built in the main body of a server, or may be provided separately from the main body of a server and be connected to the main body of the server through a cable or a network.

The memory 22 is a work memory required when the CPU 21 executes processing, and is a random access memory (RAM). The CPU 21 performs overall control of each unit of the computer by loading the control program stored in the storage device 23 to the memory 22 and executing the processing according to the program. The communication I/F 24 is a network interface for transmission control through the network 14.

A client program, such as electronic medical record software for performing the viewing or editing of electronic medical records or viewer software for performing the viewing of an examination image or the display screen 15, is installed in the medical assistance client 12 as the AP 30. For example, the viewer software is dedicated software that conforms to the specifications (commands, communication data format, and the like) suitable for the medical assistance server 11. A screen template of the display screen 15 is also included in the viewer software. Here, the medical assistance client 12 corresponds to a medical assistance device in the present embodiment.

Figure 5:
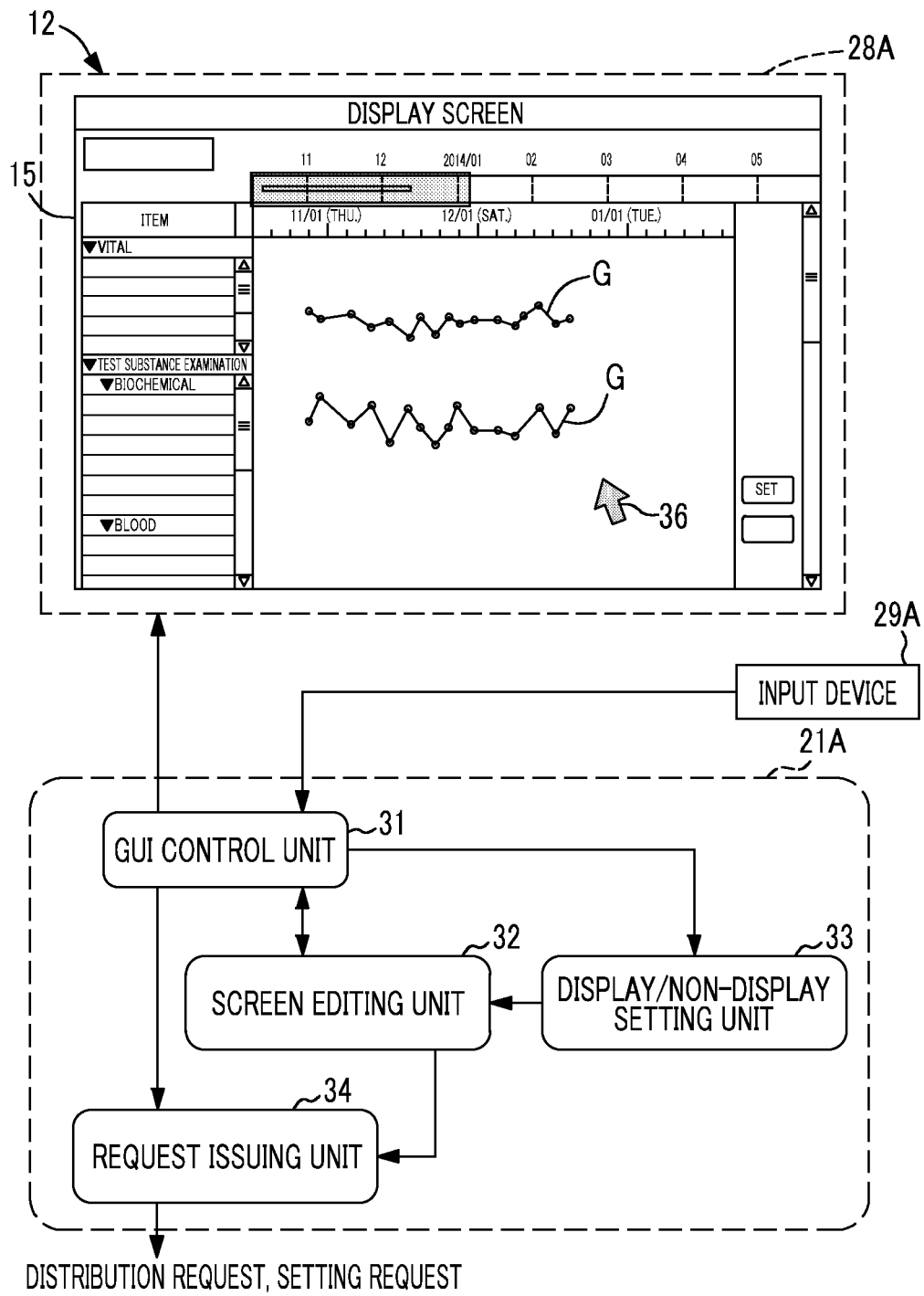
FIG. 5 is an explanatory diagram showing the functional overview of a client terminal.

As shown in FIG. 5, when the viewer software for displaying the display screen 15 is started in the medical assistance client 12, a CPU 21A of the medical assistance client 12 cooperates with the memory 22 and the like to function as a graphical user interface (GUI) control unit 31, a screen editing unit 32, a display/non-display setting unit 33, and a request issuing unit 34.

The screen editing unit 32 edits screen data of the display screen 15 based on the screen template and the medical information acquired from the medical assistance server 11. The screen editing unit 32 creates a startup screen immediately after the start of the viewer software. The startup screen is the display screen 15 that is based on only the screen template and does not include medical information, for example. An operation instruction, such as the designation of a patient ID and a medical information distribution instruction, is given on the startup screen, and the distribution of the medical information of the designated patient is received from the medical assistance server 11. Communication with the medical assistance server 11 is performed through the communication I/F 24 under the control of the CPU 21A.

The screen data edited by the screen editing unit 32 is transmitted to the GUI control unit 31. The GUI control unit 31 reproduces the display screen 15 based on the screen data, and displays the reproduced display screen 15 on a display 28A. The display screen 15 has an operation function based on the graphical user interface (GUI). On the display screen 15, a pointer 36 that is a component of the GUI is displayed. As is well known, the pointer 36 is for pointing at any position on the display screen 15, and an input device 29A, such as a mouse, functions as the operation unit. As the operation unit of the pointer 36, there is not only the mouse but also a trackball, a touch pad, and the like.

The GUI control unit 31 functions as a screen control unit that receives an operation instruction (signal of an operation instruction) input from the input device 29A through the display screen 15 and performs screen control according to the received operation instruction. For example, when the input device 29A (operation unit of the pointer 36) is a mouse, operation instructions input from the input device 29A to the GUI control unit 31 through the pointer 36 include a mouse click operation (first operation) and a mouse-over operation (second operation).

The click operation is an operation of pressing an operation button on the display screen 15 by the mouse click operation (first operation) after overlapping the pointer 36 on the operation button or the like provided on the display screen 15. On the other hand, the mouse-over operation (second operation) is an operation of overlapping the pointer 36 on the operation button or the like on the display screen 15, and is an operation that does not include the mouse click operation.

For the first and second operations, in this example, a case in which an operation unit of the pointer 36 is a mouse will be described as an example. However, even if the operation unit of the pointer 36 is a trackball, a touch pad, or the like, the first and second operations are possible. Even if the operation unit of the pointer 36 is a trackball or a touch pad, a click function using the trackball or the touch pad is provided. In addition, since the function of moving the pointer 36 is the same as the mouse, the same operation as the mouse-over operation is also possible. Although the click operation has been described as an example of the first operation in this example, the first operation may include the click operation, or may be a composite operation including a certain operation in addition to the click operation.

The display/non-display setting unit 33 is a setting unit for setting the display or non-display of items of medical information on the display screen 15. The setting of display or non-display is performed based on the operation instruction input through the GUI control unit 31. The setting information of the display/non-display setting unit 33 is transmitted to the screen editing unit 32. The screen editing unit 32 updates the screen data of the display screen 15 based on the received setting information.

The setting information is also transmitted to the medical assistance server 11. The medical assistance server 11 distributes the setting information together with the medical information when distributing the medical information subsequently. Therefore, even if the setting information is not stored in the medical assistance client 12, the setting information can be transmitted at the subsequent start. In addition, even when the medical information of the same patient is displayed in another medical assistance client 12, the setting information can be taken over through the medical assistance server 11.

The request issuing unit 34 issues a medical information distribution request or a display/non-display setting request for the medical assistance server 11. When a medical information distribution instruction is received together with the designation of a patient ID and a disease ID through the GUI control unit 31, the request issuing unit 34 issues a medical information distribution request. In addition, when the content set by the display/non-display setting unit 33 is received through the screen editing unit 32, the request issuing unit 34 issues a setting request. The issued distribution request or setting request is transmitted to the medical assistance server 11 through the network 14.

Figure 6:
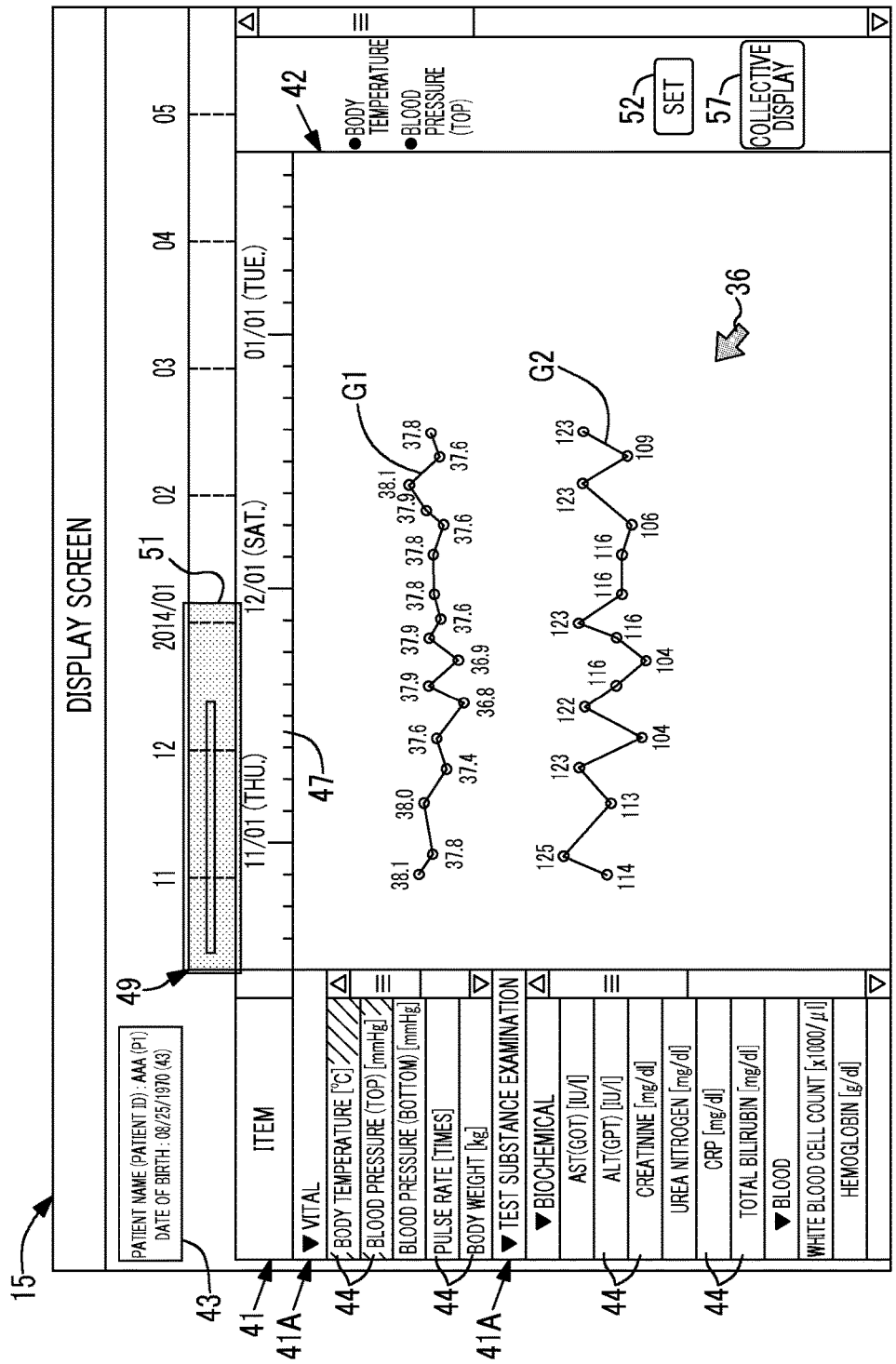
FIG. 6 is an explanatory diagram showing an example of a display screen.

As shown in FIG. 6, the display screen 15 includes an item name display region 41, a content display region 42, and a basic patient information display region 43. Basic patient information, such as a patient name, a patient ID, and age, is displayed in the basic patient information display region 43. Designation of a patient ID is performed by entering the patient name or the patient ID in the basic patient information display region 43, for example. In addition, a disease name of a patient may be displayed in the basic patient information display region 43.

The item name display region 41 is a region where item names of a plurality of items included in the medical information are listed. Item names of all items that are recorded for each patient are displayed in the item name display region 41. A display field 44 for displaying the item name for each item is provided in the item name display region 41. The item name display region 41 is divided into major categories, such as "vital" and "test substance examination", and a sub-region 41A is set for each major category. A slide bar is provided next to each sub-region 41A, so that vertical scrolling is possible for each sub-region 41A.

In this example, five items of body temperature, blood pressure (top), blood pressure (bottom), pulse rate, and body weight are displayed in the sub-region 41A of the major category "vital". Next to each item name, the unit of the data content for each item is displayed. For example, [times] is displayed in the case of a pulse rate, and [kg] is displayed in the case of body weight. Although the five items are displayed in FIG. 6, it is possible to display hidden items by vertical scrolling.

In the sub-region 41A of the major category "test substance examination", items relevant to the middle category "biochemical test" and items relevant to the middle category "blood test" are included. The items of the biochemical test are, for example, six items of AST (GOT), ALT: alanine aminotransferase (GPT: glutamic pyruvic transaminase), creatinine, urea nitrogen, CRP: C-reactive protein, and total bilirubin, and the items of the blood test are a white blood cell count, hemoglobin, and the like. Also for the sub-region 41A of the test substance examination, it is possible to display hidden items by scrolling.

The content display region 42 is a region where the data content of each item of medical information, such as body temperature or blood pressure, is displayed. In the content display region 42, time is assigned to the horizontal axis, and time-series data showing the temporal transition of the data content is displayed in the form of graphs G1 and G2, for example. Each of the graphs G1 and G2 is a line graph obtained by connecting the input points of a plurality of pieces of data in the form of a line segment, and the numerical value of the data is displayed at each input point. Therefore, it is possible to check changes in the conditions of a patient over time. In addition to the numerical data, it is also possible to display image data, such as an examination image, in the content display region 42. As an examination image, a thumbnail image is displayed at a position corresponding to the imaging date.

A first time axis 47 is provided at the top of the content display region 42. The first time axis 47 is obtained by arranging markings and information, such as year, month, and day, according to the set time scale. The first time axis 47 has a length corresponding to the first display period of the content display region 42, and has a width in the vertical direction so that information can be displayed therein. In this example, the first display period is set to about four months from the end of October, 2013 to the middle of January, 2014.

The first display period can be changed by the screen scrolling operation in the horizontal direction. By the screen scrolling operation, the display range of medical information is changed, and accordingly, the display of year and month on the first time axis 47 is also changed. In the content display region 42, screen scrolling in the vertical direction is also possible. When there is a hidden graph G, it is possible to display the graph G by the screen scrolling operation in the vertical direction.

A second time axis 49 having a longer time scale than the first time axis 47 is provided above the first time axis 47. The second time axis 49 indicates a second display period longer than the first display period. In this example, the second display period is set to about eight months, which is twice the first display period (four months). On the second time axis 49, markings are displayed monthly, for example. On the second time axis 49, the first display period is included. In addition, a period indicator 51 showing the first display period is displayed on the second time axis 49. The period indicator 51 is an indicator showing to which period the first display period of the content display region 42 corresponds on the second time axis 49. The width of the period indicator 51 corresponds to the width of the first display period in the time scale of the second time axis 49. In this example, since the first display period is about four months, the width of the period indicator 51 corresponds to the width for about four months in the time scale of the second time axis 49.

In addition, items displayed in the content display region 42 are display setting items, of which display setting is performed by the display/non-display setting unit 33, among the items displayed in the item name display region 41. In this example, two items of body temperature and blood pressure (top) of vital are display setting items. The graph G1 indicates body temperature, and the graph G2 indicates blood pressure (top). As shown in the item name display region 41, there are many items of medical information. Accordingly, when all items are displayed, graphs of the items overlap each other and it is difficult to see the graphs. For this reason, a good view of the high-priority items can be ensured by performing display setting only for items that particularly need to be displayed at all times, for example, only for high-priority items that should be checked at all times and performing non-display setting for other items.

In the item name display region 41, the display field 44 of the display setting item (body temperature and blood pressure (top)) is displayed in an identifiable form by setting the color or concentration different from the other display fields 44, for example, by hatching. On the right side of the content display region 42, item names of the display setting items are displayed. Through such display, it is possible to easily check which item is a display setting item.

A setting button 52 is a button for performing various settings, and there is a display/non-display setting for each setting. When the setting button 52 is operated and the display/non-display setting is selected from the setting menu, a setting screen 53 shown in FIG. 7 is displayed. All items displayed in the item name display region 41 are displayed on the setting screen 53, and it is possible to perform a display/non-display setting for each item. The display/non-display setting is performed by checking a check box 53A by performing a click operation (first operation) in a state in which the pointer 36 is positioned so as to overlap the desired check box 53A by movement of a mouse.

In this example, since the two items of body temperature and blood pressure (top) are set to be displayed, the display check boxes 53A for the two items are checked, and the non-display check boxes 53A for other items are checked. The display/non-display setting operation in this example is just an example, and other methods may also be used. For example, check boxes may be provided for each display field 44 of the item name display region 41 without using the setting screen 53, so that the display/non-display setting is performed by the mouse click operation (first operation).

Although the display/non-display setting for each item is performed as described above, the display screen 15 further has a function of temporarily displaying non-display setting items, which are set so as not to be displayed, by the mouse-over operation (second operation).

Figure 8:
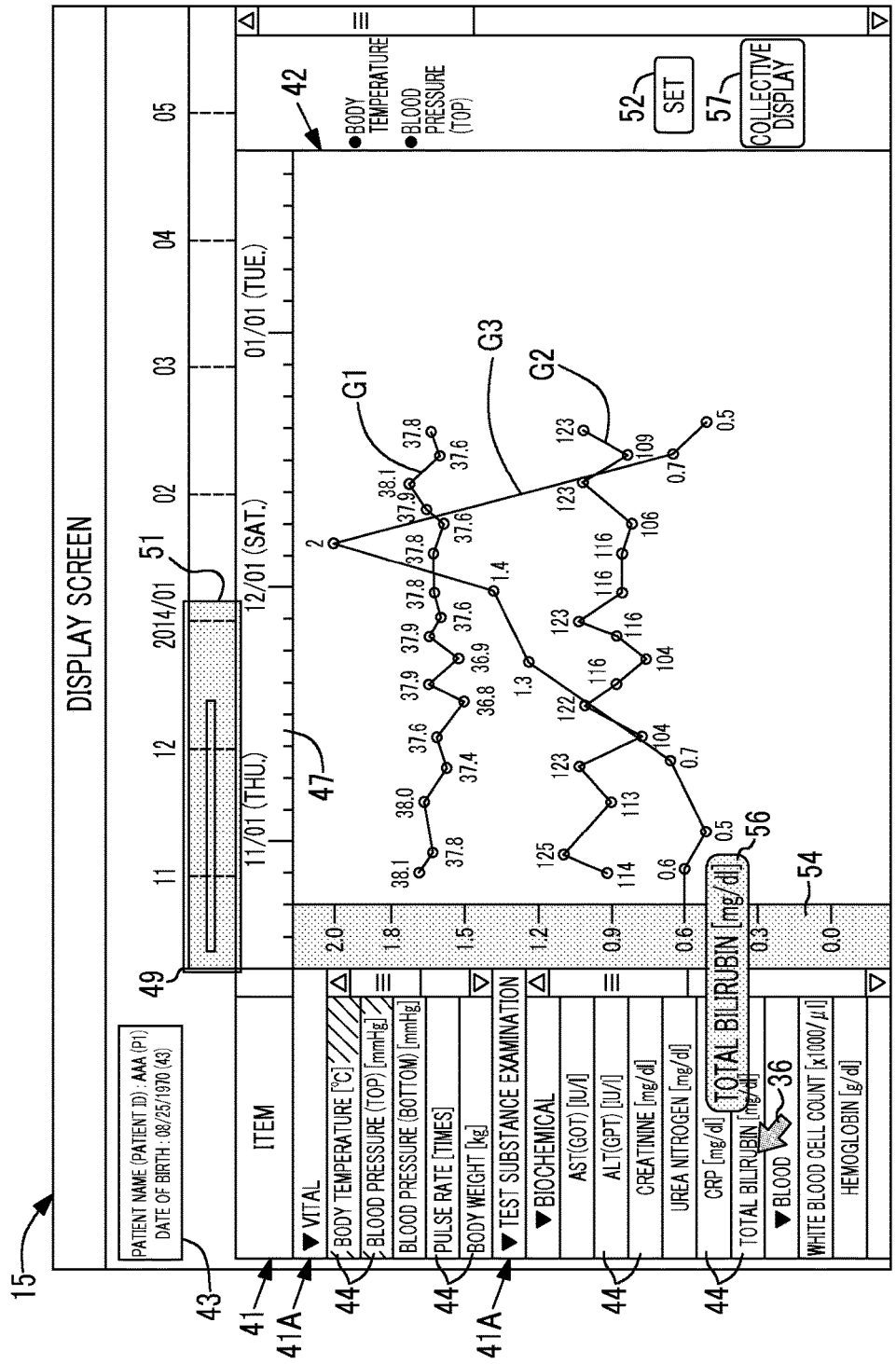
FIG. 8 is an example of a display screen on which a non-display setting item is displayed by a mouse-over operation.

Specifically, as shown in FIG. 8, data content corresponding to the display field 44 of an item name that the pointer 36 overlaps is displayed in the content display region 42 by performing a mouse-over operation without a mouse click operation just by overlapping the pointer 36 on the display field 44 of a desired item name in the item name display region 41 through the mouse moving operation. When the pointer 36 deviates from the position of the display field 44 of the item name and the mouse-over operation ends, the data content is returned to the non-display state.

In the example shown in FIG. 8, the mouse-over operation is performed on the display field 44 having an item name of total bilirubin. Accordingly, in the content display region 42, a graph G3 that is the data content of total bilirubin set so as not to be displayed is displayed in addition to the graphs G1 and G2 set to be displayed. When the pointer 36 deviates from the display field 44 of total bilirubin, the graph G3 of total bilirubin is not displayed again. While the graph G3 is displayed, markings 54 of total bilirubin are displayed on the vertical axis on the left end of the content display region 42. When the graph G3 is not displayed, the markings 54 also disappear.

By enabling the temporary display of a non-display setting item through the mouse-over operation, it is possible to refer to the non-display setting item temporarily by the simple operation.

Such screen control is performed by the GUI control unit 31. The GUI control unit 31 monitors the position of the pointer 36 in the display screen 15, and determines that the mouse-over operation has been performed when it is detected that the pointer 36 overlaps one of the display fields 44 of the item names, which are set as non-display items, in the item name display region 41. The GUI control unit 31 displays the graph G3 corresponding to the item name for which the mouse-over operation has been performed. In this case, medical information of non-display setting items may not be distributed in advance from the medical assistance server 11. In this case, the GUI control unit 31 transmits a distribution request to the medical assistance server 11 through the request issuing unit 34, and acquires the required medical information. The screen editing unit 32 is started, when necessary, to edit the display screen 15.

In addition, the GUI control unit 31 performs pop-up display of a tag 56 for the display field 44 that the pointer 36 overlaps in the item name display region 41. The tag 56 is intended to display the item name that is pointed to by the pointer 36. In this example, the tag 56 of total bilirubin pops up. As in this example, when there is no large difference between the size of the pointer 36 and the size of the display field 44, it is difficult to position the pointer 36 so as to overlap only one display field 44. In general, the pointer 36 has an arrow shape. An object is pointed to by overlapping the distal end of the pointer 36 on the object. Also in this example, the pointer 36 has an arrow shape. Therefore, the GUI control unit 31 determines that the display field 44 that the distal end of the pointer 36 overlaps is an object to be pointed to, and displays the tag 56 for the display field 44 determined to be the object. In this manner, even when the pointer 36 overlaps the display fields 44 of a plurality of item names, it is possible to easily check which display field 44 the object pointed to by the pointer 36 is.

Figure 9:
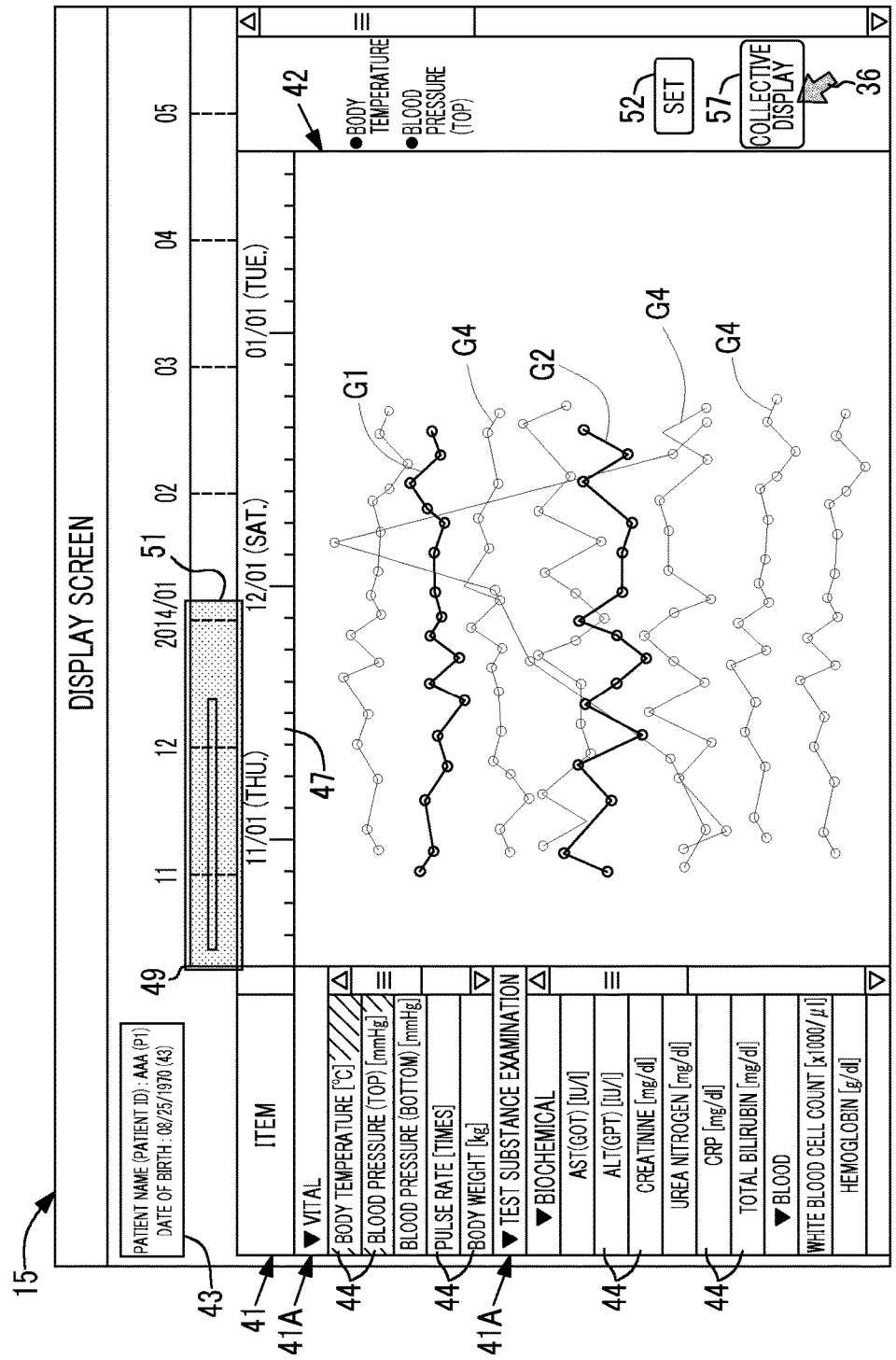
FIG. 9 is an example of a display screen when non-display setting items are set to be collectively displayed.

In addition, a collective display button (collective display operation unit) 57 is provided on the display screen 15. The collective display button 57 is an operation unit for inputting an operation instruction to display the data content of all of the non-display setting items collectively while maintaining the setting content of the non-display setting items. When the collective display button 57 is clicked, not only the graphs G1 and G2 of display setting items but also graphs G4 of all of non-display setting items are displayed in the content display region 42, as shown in FIG. 9. In this case, since the setting content that has been set by the display/non-display setting unit 33 is not changed, the setting content of the non-display setting items is not still displayed.

In the content display region 42, the graphs G1 and G2 of the display setting items and the graphs G4 of the non-display setting items are displayed so as to be distinguishable. Specifically, since the high-priority items are graphs G1 and G2, the graph G4 is displayed in gray when the graphs G1 and G2 are displayed in black, for example. Thus, by using a method of lowering the concentration of the graph G4 relative to that of the graphs G1 and G2 or the like, the graph G4 is made to be inconspicuous relative to the graphs G1 and G2. Therefore, even if non-display setting items are collectively displayed, it is possible to distinguish the non-display setting items from display setting items. When the collective display button 57 is clicked again, the non-display setting items are not displayed again.

Figure 10:
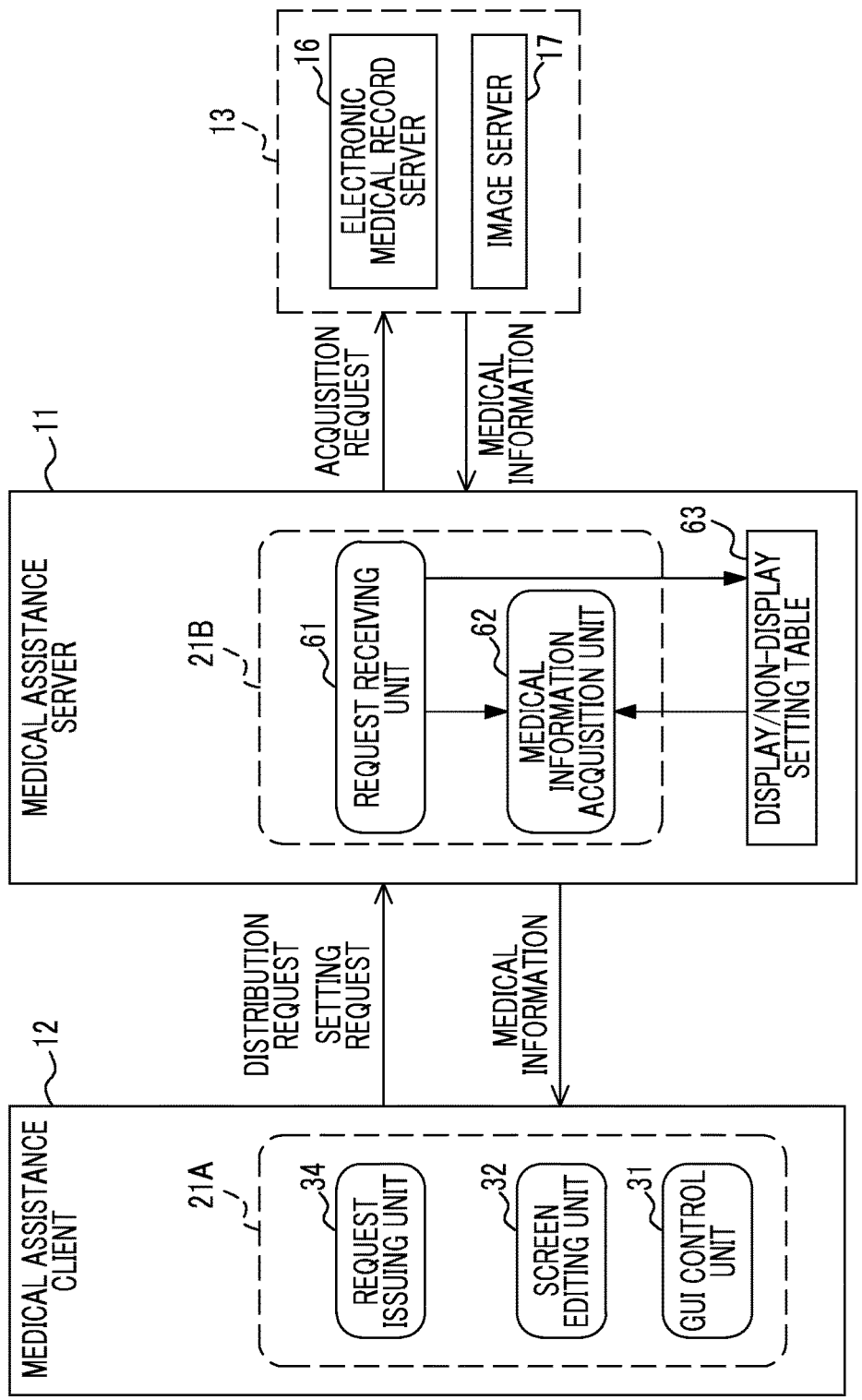
FIG. 10 is a schematic diagram of the process of the medical assistance client and the medical assistance server.

As shown in FIG. 10, in the medical assistance server 11, a server program for making the medical assistance server 11 function as a medical assistance server is installed as the AP 30. When a CPU 21B of the medical assistance server 11 starts the server program, the CPU 21B functions as a request receiving unit 61 and a medical information acquisition unit 62. The request receiving unit 61 receives a distribution request or a setting request from the medical assistance client 12. The medical information acquisition unit 62 transmits an acquisition request for the medical information of a patient, who has been designated in the distribution request, to the server group 13, and acquires the medical information.

When the request receiving unit 61 receives a setting request, the setting information is stored in a display/non-display setting table 63. The display/non-display setting table 63 is a storage unit for storing the setting information for each patient set by the display/non-display setting unit 33 of the medical assistance client 12. When distributing the medical information to the medical assistance client 12, the medical information acquisition unit 62 checks the presence of setting information regarding the designated patient with reference to the display/non-display setting table 63. When there is setting information, the setting information is distributed to the medical assistance client 12 together with the medical information.

Figure 11:
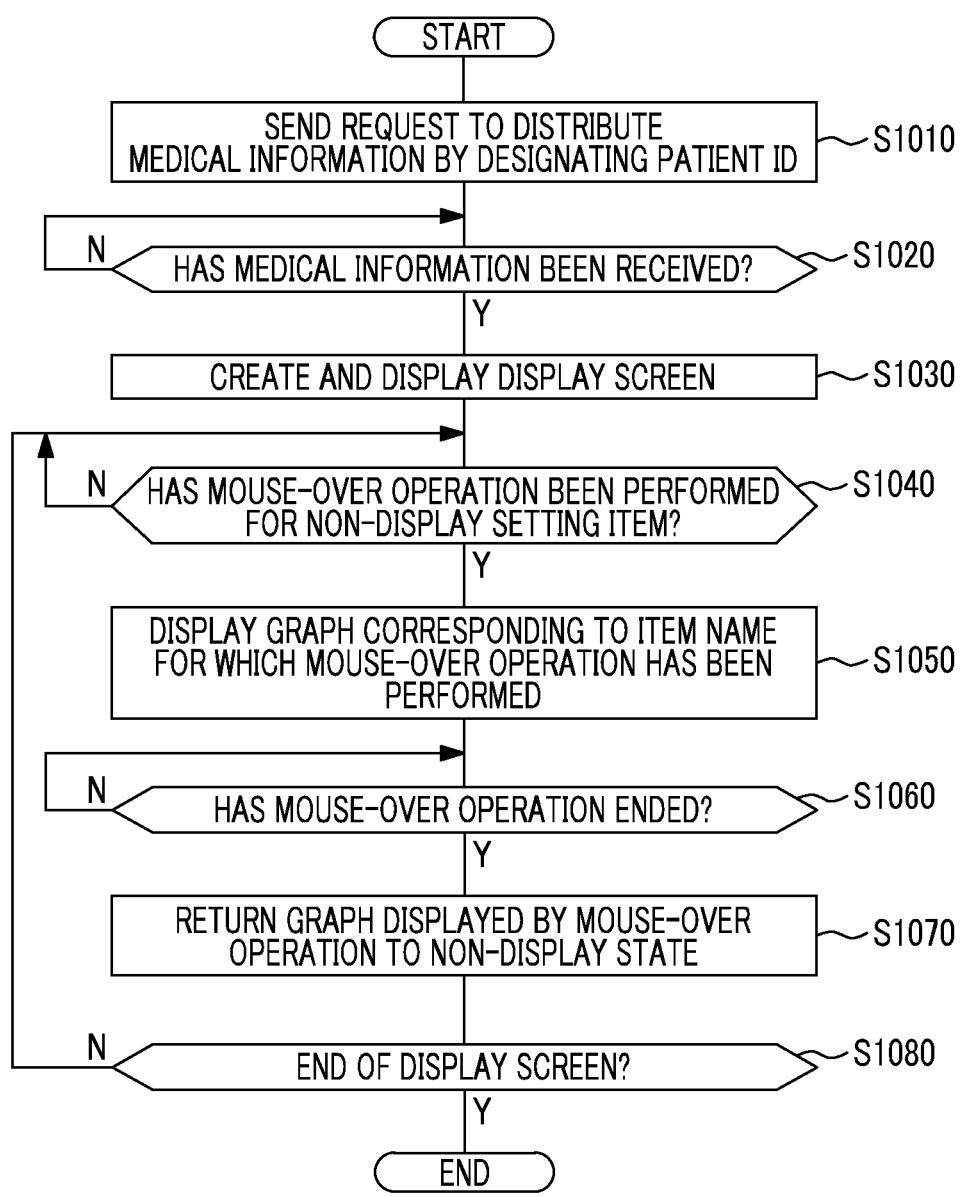
FIG. 11 is a flowchart showing the display procedure of medical information.

Hereinafter, the operation of the above configuration will be described with reference to FIG. 11. When viewing the medical information using the medical assistance client 12, viewer software for viewing the medical information is started. Then, a request to distribute the medical information is given by designating the patient ID through the display screen 15 that functions as an operation screen (S1010). The medical assistance server 11 distributes the medical information of the designated patient to the medical assistance client 12 based on the distribution request.

When the medical assistance client 12 receives the medical information (Y in S1020), the screen editing unit 32 creates screen data of the display screen 15 based on the received medical information. When the setting information regarding the display/non-display is stored in the medical assistance client 12 or when the setting information is received together with the medical information, the screen editing unit 32 determines display setting items, among the items of the received medical information, based on the setting information, and creates screen data of the display screen 15 to display only the display setting items as the data content. As shown in FIG. 6, the GUI control unit 31 reproduces the display screen 15 based on the screen data created by the screen editing unit 32, and displays the reproduced display screen 15 on the display 28A (S1030).

In the display screen 15 in the initial state shown in FIG. 6, only the graphs G1 and G2 of display setting items are displayed and the graphs of non-display setting items are not displayed in the content display region 42. Therefore, since only the high-priority items that should be displayed at all times are displayed, good visibility is ensured for the high-priority items. On the other hand, depending on the circumstances of diagnosis, such as the condition of a patient or the progress of a disease, even a non-display setting item needs to be temporarily displayed for reference. In such a case, by performing a mouse-over operation for overlapping the pointer 36 on a desired item name, the data content corresponding to the item name can be temporarily displayed.

The GUI control unit 31 monitors the display field 44 of which item name in the item name display region 41 the pointer 36 overlaps based on the position of the pointer 36, and detects whether or not a mouse-over operation has been performed for a non-display setting item (S1040). When the mouse-over operation has been detected (Y in S1040), the GUI control unit 31 displays the graph G3 corresponding to the item name as shown in FIG. 8 (S1050). Therefore, the doctor can also refer to the data content of the non-display setting item by a simple operation called the mouse-over operation. Since the mouse-over operation is an operation that does not include the click operation, such as the change of the setting content using the setting button 52, the operation is simple.

Not only is the click operation complicated compared with the mouse-over operation, but also the number of operations is increased when viewing continues for a long period time and accordingly the physical burden, such as a burden on the shoulder, is very large. Therefore, it is possible to greatly reduce the physical burden by adopting the mouse-over operation.

In addition, when the graph G3 is displayed, the markings 54 corresponding to the graph G3 are displayed. Through the markings 54, it becomes easy to check the numerical values of the graph G3.

After checking the graph G3 of the non-display setting item, the doctor removes the pointer 36 from the display field 44 of the item name to end the mouse-over operation. When it is detected that the pointer 36 has been removed from the display field 44 of the item name and the mouse-over operation has ended (Y in S1060), the GUI control unit 31 returns the graph G3 displayed by the mouse-over operation to the non-display state (S1070). Thus, by a simple operation of removing the pointer 36 from the item name, it is possible to return to the original state in which the data content of the non-display setting item is not displayed.

On the display screen 15, it is also possible to display all of the non-display setting items as shown in FIG. 9 using the collective display button 57. In this case, the non-display setting items are displayed so as to be inconspicuous relative to the display setting items. Therefore, it is possible to distinguish between the display setting items and the non-display setting items and to reduce a lowering in the visibility of the display setting items.

Thus, according to the present embodiment, on the display screen 15 to display a plurality of items of medical information, it is possible to refer to the non-display setting item temporarily by the simple operation.

In this example, display forms, such as the layout of the display screen 15, are examples, and various modifications are possible.

Second Embodiment

Figure 12:
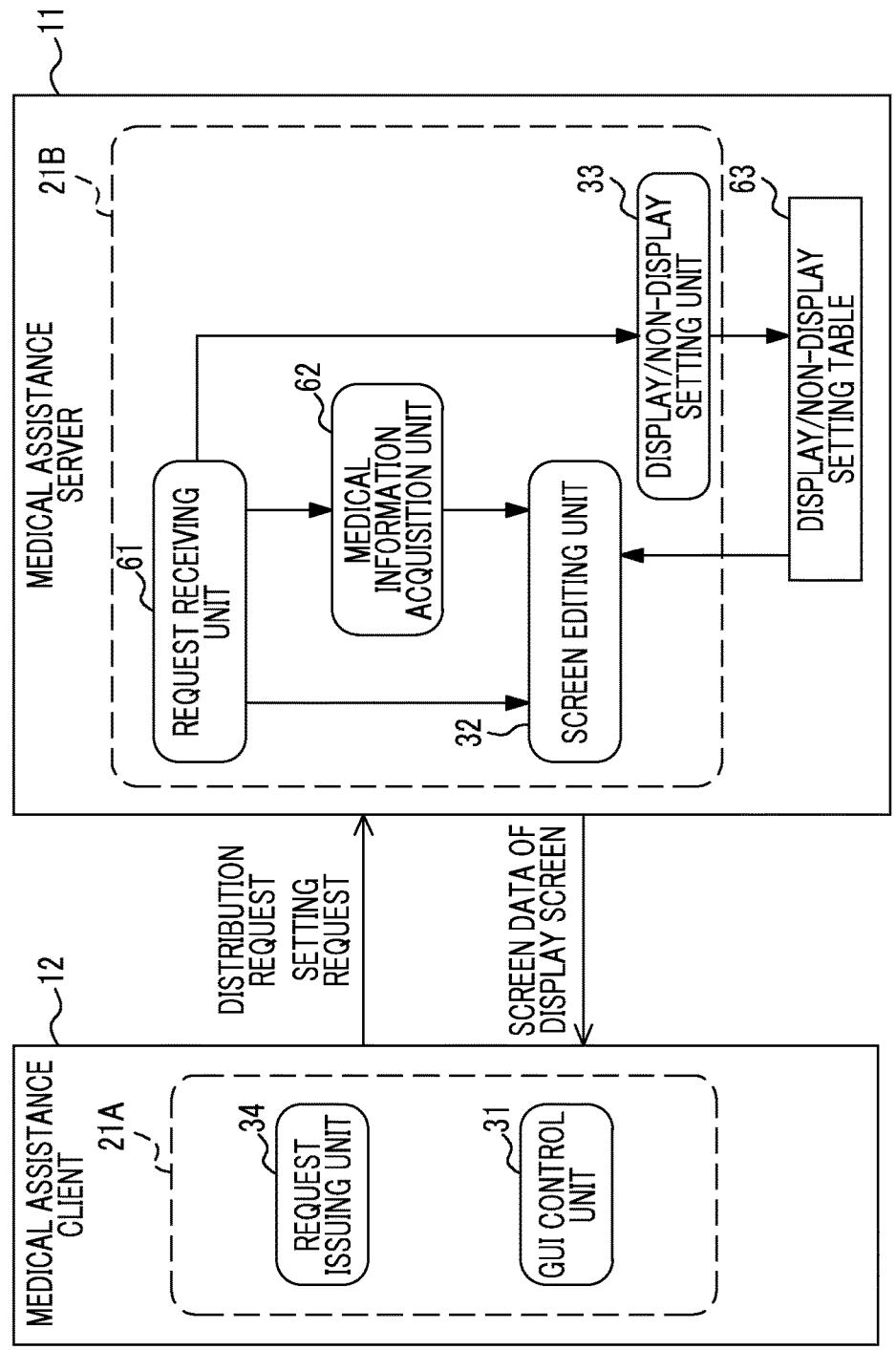
FIG. 12 is an explanatory diagram of a second embodiment.

In the first embodiment, an example has been described in which the medical assistance client 12 is a medical assistance device. However, as shown in FIG. 12, the medical assistance server 11 can be made to function as a medical assistance device. In this case, the screen editing unit 32, and the display/non-display setting unit 33 are provided in the medical assistance server 11.

The medical assistance server 11 creates screen data of the display screen 15 using the screen editing unit 32, and distributes the created screen data to the medical assistance client 12. For example, the screen data is data written in a markup language, such as Extensible Markup Language (XML). A general-purpose WEB browser is installed in the medical assistance client 12. Using the general-purpose WEB browser, the GUI control unit 31 reproduces the display screen 15 based on the received screen data, and displays the reproduced display screen 15 on the display 28A. The GUI control unit 31 transmits an input operation instruction, such as a click operation or a mouse-over operation, to the medical assistance server 11. The screen editing unit 32 of the medical assistance server 11 edits the display screen 15 based on the received operation instruction, and distributes the edited screen data to the medical assistance client 12. When the medical assistance server 11 functions as a medical assistance device, the screen editing unit 32 in the medical assistance server 11 functions as a screen control unit.

In addition, a medical assistance system formed by the medical assistance server 11 and the medical assistance client 12 may be made to function as a medical assistance device, instead of each of the medical assistance server 11 and the medical assistance client 12 that functions as a medical assistance device independently as in the first and second embodiments. In this case, some of the components of the medical assistance device are provided in each of the medical assistance server 11 and the medical assistance client 12.

Thus, the medical assistance device of the invention can be implemented in various ways. In addition, the hardware configuration of a computer system, such as the medical assistance server 11 and the medical assistance client 12, can be modified in various ways. For example, in order to improve the capacity or reliability, the medical assistance server 11 may be configured by a plurality of server computers that are separated from each other as hardware. Thus, the hardware configuration of a computer system can be appropriately changed according to the required performance, such as capacity, safety, or reliability. Needless to say, in order to ensure the safety or reliability, a basic program or a diagnostic assistance program may be duplicated or may be stored in a plurality of storage devices so as to be distributed, without being limited to hardware.

In each of the above embodiments, an example has been described in which medical assistance devices are used in one medical facility. However, for example, one medical assistance server 11 may be installed in an external data center so that a plurality of medical facilities can use the medical assistance server 11 in the data center.

The medical assistance server 11 is communicably connected to the medical assistance client 12 installed in each of the plurality of medical facilities, for example, through a wide area network (WAN), such as the Internet or a public communication network. The medical assistance server 11 receives requests from the medical assistance clients 12 in the plurality of medical facilities, and distributes medical information or diagnostic assistance information to each client terminal or provides application services for association setting to each client terminal.

The locations or management entity of the data center and the medical assistance server 11 may be one of the plurality of medical facilities, or may be a separate service company from the medical facilities, for example. When using a WAN, such as a network, it is preferable to build a virtual private network (VPN) or to use a communications protocol with a high security level, such as hypertext transfer protocol secure (HTTPS), in consideration of information security.

It is needless to say that the invention is not limited to the above embodiments and various configurations can be adopted without departing from the scope of the invention. For example, it is also possible to appropriately combine the above-described various embodiments or various modifications. In addition to the program, the invention also extends to a storage medium for storing the program.

What is claimed is:
1. A medical assistance device, comprising:
a processor configured to:
edit a display screen for displaying medical information of a patient and send an operation instruction by operating a pointer of a graphical user interface, the display screen having an item name display region where an item name of each of a plurality of items included in the medical information is displayed and a content display region where data content for each of the items is displayed, wherein the data content for each of the items comprises numerical data in different data ranges and units;
configure at least one of the items listed in the item name display region as selected item in response to the operation instruction based on a first operation including a click operation of an operation unit of the pointer;
perform control to display the data content corresponding to the selected item as a first trend line in a medical trend graph in the content display region;
perform control to simultaneously display, with the first trend line in the medical trend graph in the content display region, the data content corresponding to non-selected item listed in the item name display region, on which the pointer is in a position overlaps with, as a second trend line in the medical trend graph in the content display region in response to the operation instruction based on a second operation not including the click operation and to return the data content corresponding to the non-selected item to a non-display state when the pointer is removed from the position overlapping with the non-selected item, and
wherein when the second trend line of the non-selected item is displayed by the second operation, markings indicating the numerical data of the data content corresponding to the non-selected item are modified and displayed in the content display region, and the second trend line is maximized in the content display region and overlapping with the first trend line; and
receive an operation instruction performed on a collective display button provided on the display screen to collectively display the data content in the content display region for all of the items listed in the item name display region while maintaining setting of configuring the at least one items listed in the item name display region as selected item for display.

2. The medical assistance device according to claim 1, wherein the data content is time-series data for each of the items in which medical information of the patient is recorded in time series.

3. The medical assistance device according to claim 1, wherein the data content is time-series data for each of the items in which medical information of the patient is recorded in time series.

4. The medical assistance device according to claim 2, wherein the time-series data is displayed in a form of a graph.

5. The medical assistance device according to claim 3, wherein the time-series data is displayed in a form of a graph.

6. The medical assistance device according to claim 2, wherein the items include items regarding vital signs and examinations.

7. The medical assistance device according to claim 3, wherein the items include items regarding vital signs and examinations.

8. The medical assistance device according to claim 2, wherein, on the display screen, a plurality of the item names are arranged in a vertical direction in the item name display region, a time axis is set in a horizontal direction in the content display region, and the time-series data is displayed for each of the items.

9. The medical assistance device according to claim 3, wherein, on the display screen, a plurality of the item names are arranged in a vertical direction in the item name display region, a time axis is set in a horizontal direction in the content display region, and the time-series data is displayed for each of the items.

10. The medical assistance device according to claim 4, wherein, on the display screen, a plurality of the item names are arranged in a vertical direction in the item name display region, a time axis is set in a horizontal direction in the content display region, and the time-series data is displayed for each of the items.

11. An operation method of a medical assistance device, comprising:
- a screen editing step of editing a display screen for displaying medical information of a patient and sending an operation instruction by operating a pointer of a graphical user interface, the display screen having an item name display region where an item name of each of a plurality of items included in the medical information is displayed and a content display region where data content for each of the items is displayed, wherein the data content for each of the items comprises numerical data in different data ranges and units;
- a display and non-display setting step of configuring at least one of the items listed in the item name display region as selected item in response to the operation instruction based on a first operation including a click operation of the pointer;
- a screen control step of performing control to simultaneously display the data content corresponding to the selected item as a first trend line in a medical trend graph in the content display region and the data content corresponding to non-selected item listed in the item name display region, on which the pointer is in a position overlaps with, as a second trend line in the medical trend graph in the content display region in response to the operation instruction based on a second operation not including the click operation and to return the data content corresponding to the non-selected item to a non-display state when the pointer is removed from the position overlapping with the non-selected item, and
- wherein when the second trend line of the non-selected item is displayed by the second operation, markings indicating the numerical data of the data content corresponding to the non-selected item are modified and displayed in the content display region, and the second trend line is maximized in the content display region and overlapping with the first trend line: and
- a collective display step of receiving an operation instruction performed on a collective display button provided on the display screen to collectively display the data content in the content display region for all of the items listed in the item name display region while maintaining setting of configuring the at least one item listed in the item name display region as selected item for display.

12. A non-transitory computer-readable recording medium on which a medical assistance program causing a computer to function as a medical assistance device is recorded, the program causing the computer to execute:
- a screen editing step of editing a display screen for displaying medical information of a patient and sending an operation instruction by operating a pointer of a graphical user interface, the display screen having an item name display region where an item name of each of a plurality of items included in the medical information is displayed and a content display region where data content for each of the items is displayed, wherein the data content for each of the items comprises numerical data in different data ranges and units;
- a display and non-display setting step of configuring at least one of the items listed in the item name display region as selected item in response to the operation instruction based on a first operation including a click operation of the pointer;
- a screen control step of performing control to simultaneously display the data content corresponding to the selected item as a first trend line in a medical trend graph in the content display region and the data content corresponding to non-selected item listed in the item name display region, on which the pointer is in a position overlaps with, as a second trend line in the medical trend graph in the content display region in response to the operation instruction based on a second operation not including the click operation and to return the data content corresponding to the non-selected item to a non-display state when the pointer is removed from the position overlapping with the non-selected item, and
- wherein when the second trend line of the non-selected item is displayed by the second operation, markings indicating the numerical data of the data content corresponding to the non-selected item are modified and displayed in the content display region, and the second trend line is maximized in the content display region and overlapping with the first trend line: and
- a collective display step of receiving an operation instruction performed on a collective display button provided on the display screen to collectively display the data content in the content display region for all of the items listed in the item name display region while maintaining setting of configuring the at least one item listed in the item name display region as selected item for display.

13. A medical assistance system formed by a medical assistance client and a medical assistance server, comprising:
- a processor configured to:
- edit a display screen for displaying medical information of a patient and send an operation instruction by operating a pointer of a graphical user interface, the display screen having an item name display region where an item name of each of a plurality of items included in the medical information is displayed and a content display region where data content for each of the items is displayed, wherein the data content for each of the items comprises numerical data in different data ranges and units;
- configure at least one of the items listed in the item name display region as selected item in response to the operation instruction based on a first operation including a click operation of an operation unit of the pointer;
- perform control to display the data content corresponding to the selected item as a first trend line in a medical trend graph in the content display region;
- perform control to simultaneously display, with the first trend line in the medical trend graph in the content display region, the data content corresponding to non-selected item listed in the item name display region, on which the pointer is in a position overlaps with, as a second trend line in the medical trend graph in the content display region in response to the operation instruction based on a second operation not including the click operation and to return the data content corresponding to the non-selected item to a non-display state when the pointer is removed from the position overlapping with the non-selected item, and
- wherein when the second trend line of the non-selected item is displayed by the second operation, markings indicating the numerical data of the data content corresponding to the non-selected item are modified and displayed in the content display region, and the second trend line is maximized in the content display region and overlapping with the first trend line: and receive an operation instruction performed on a collective display button provided on the display screen to collectively display the data content in the content display region for all of the items listed in the item name display region while maintaining setting of configuring the at least one items listed in the item name display region as selected item for display.

* * * * *